United States Patent [19]

Jarofski

[11] Patent Number: 4,914,310
[45] Date of Patent: Apr. 3, 1990

[54] METHOD AND APPARATUS FOR MEASURING PARTICLE CONCENTRATION IN A SUSPENSION

[75] Inventor: Dieter Jarofski, Lithonia, Ga.

[73] Assignee: Bonnier Technology Group, Inc., Decatur, Ga.

[21] Appl. No.: 313,394

[22] Filed: Feb. 21, 1989

[30] Foreign Application Priority Data

Feb. 22, 1988 [SE] Sweden .................................. 8800599

[51] Int. Cl.$^4$ ............................................. G01N 15/06
[52] U.S. Cl. ..................................... 250/574; 250/575; 356/343
[58] Field of Search ................. 250/574, 575; 356/343, 356/342, 341, 336, 442

[56] References Cited

U.S. PATENT DOCUMENTS 3,867,033 2/1975 Hasinger ............................. 356/342

Primary Examiner—David C. Nelms
Assistant Examiner—Sherrie Hsia
Attorney, Agent, or Firm—Ostrolenk, Faber, Gerb & Soffen

[57] ABSTRACT

A method and apparatus for measuring the particle concentration of suspensions, especially suspensions having high particle concentration. Light is directed into the suspension, and light scattered by the particles, preferably back-scattered light, is detected at a first and a second position located at different distances from the position where the light is sent into the suspension. The concentration is then calculated as $$\text{arctanh } (E_f/E_n),$$

or preferably $$\tfrac{1}{2} \ln \frac{E_f + E_n}{E_n - E_f},$$

where $E_n$ is the detected light intensity at the first relatively near position and $E_f$ is the light intensity at the second relatively far position. The intensity of the light directed into the suspension is controlled by means of the relation $E_f E_n = 1$. The mean value of $E_f$ and $E_n$ is then compared with 1 in order to determine whether the calculated concentration corresponds to the concentration of the suspension being measured.

15 Claims, 4 Drawing Sheets

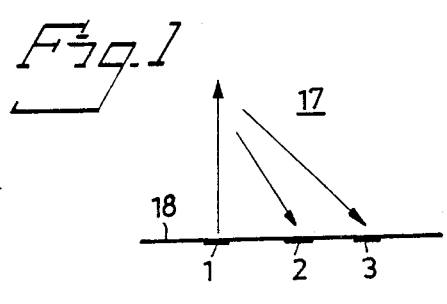
Fig. 1
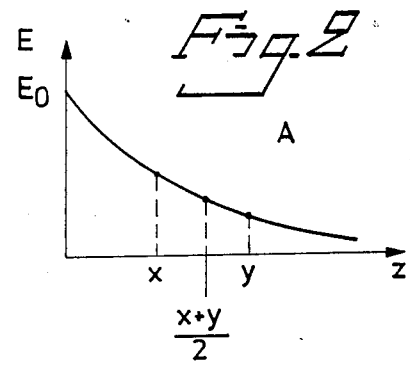
Fig. 2
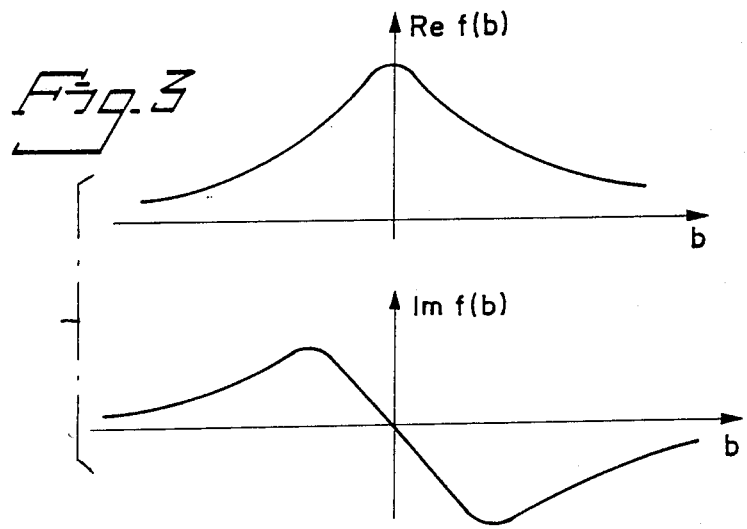
Fig. 3
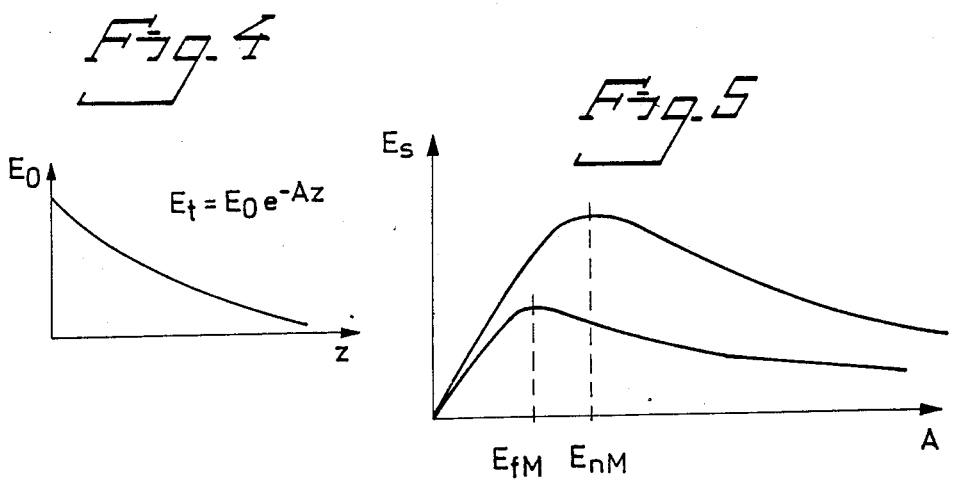
Fig. 4
Fig. 5

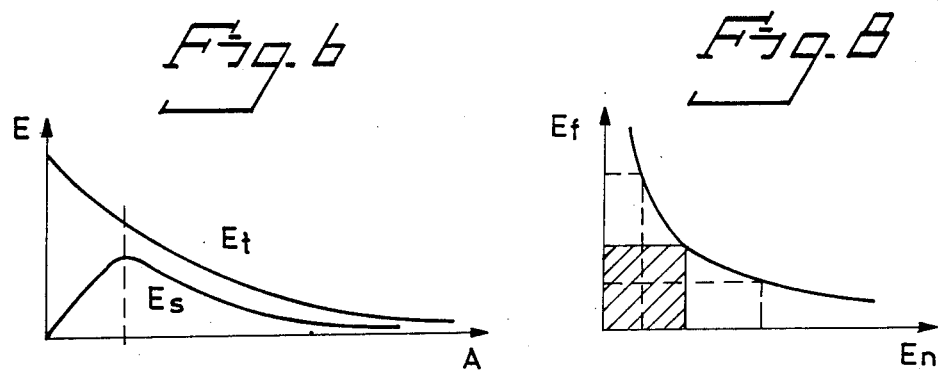
Fig. 6
Fig. 8
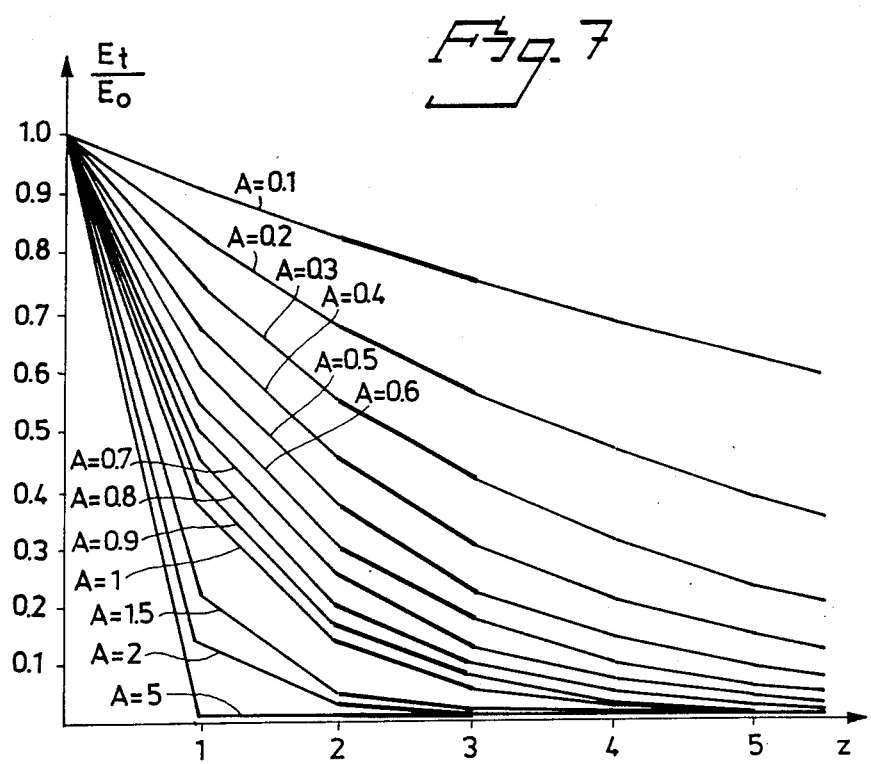
Fig. 7

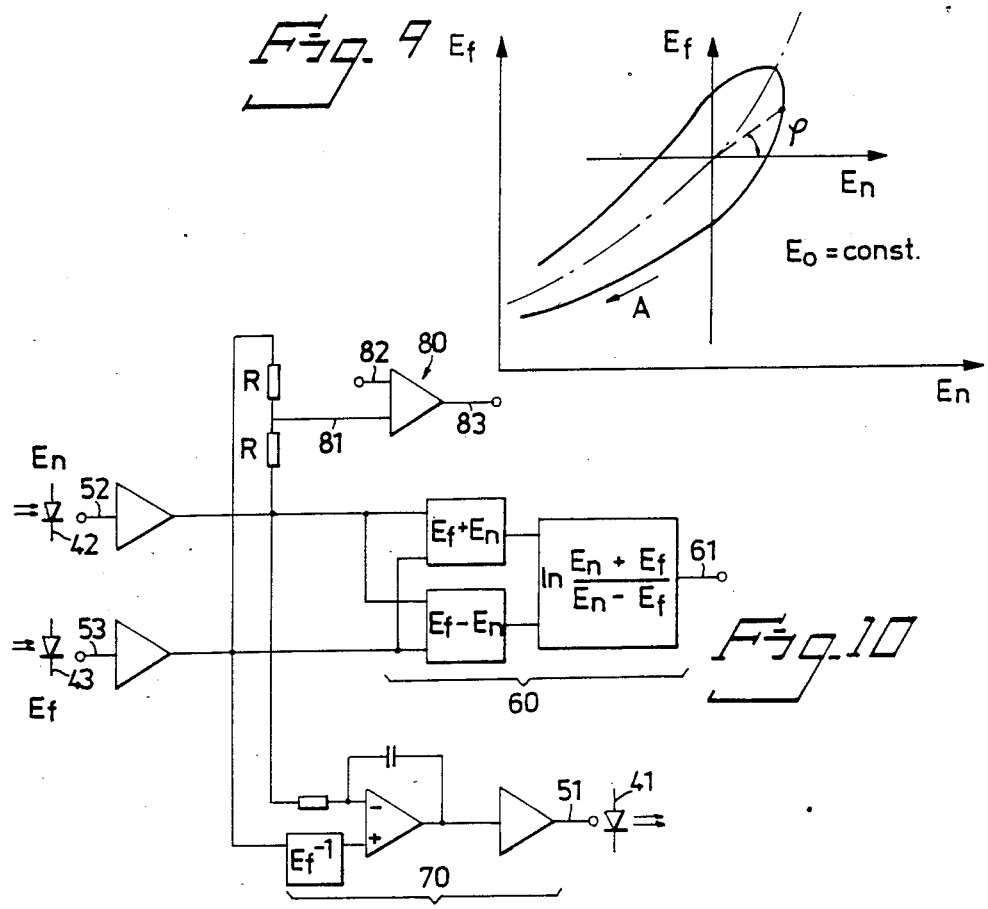
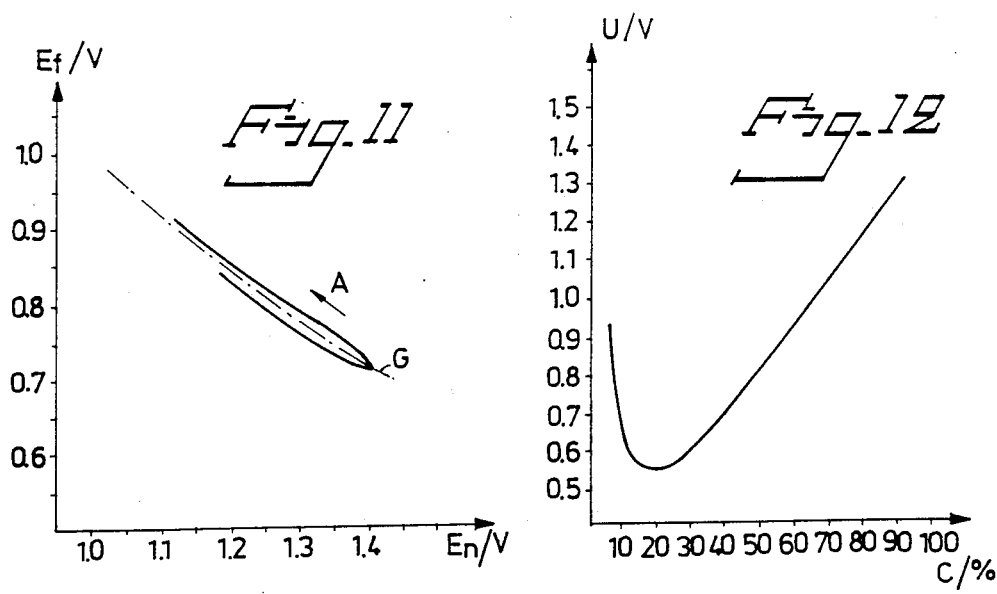

METHOD AND APPARATUS FOR MEASURING PARTICLE CONCENTRATION IN A SUSPENSION

The present refers to a method of measuring concentration of particles suspended in a fluid, comprising directing radiation energy into the fluid and measuring the intensity of the energy scattered by the particles.

The invention also refers to an apparatus for performing the method.

Various methods and apparatus of the type indicated above have been developed in order to provide continuous super vision of the particle concentration of various suspensions, but generally, it remains to provide methods and apparatus for precise measurement of the concentration, especially when the suspension has relatively high particle concentrations, and when it is desired to have an output signal which is substantially a linear function of the concentration, while using relatively uncomplicated apparatus for providing such output signals.

Therefore, an object of the invention is to provide an uncomplicated technique of measuring the concentration of particles in a particle suspension, particularly relatively high concentrations.

Another object is to provide such a technique, in which the output signal substantially is a linear function of the concentration, especially for high concentrations.

Another object is to determine whether the output signal refers to supensions in the measuring range.

Another object of the invention is to produce suitable apparatus for implementing the measuring technique.

Another object is to define dimensioning limits for the apparatus in order to avoid certain types of errors, and suitable structural features for maximizing the level of measured signals while minimizing distribution width of the measured signals.

The above objects, as well as other objects described herein or realized by the artsmen, will at least in some extent be attained by the invention.

The inventive method comprises the known steps of directing radiation energy into to suspension and measuring the intensity of the energy scattered by the particles, and is characterized by the steps of measuring the intensity at a first position located relatively near to an emission position where the energy is directed to the fluid, and also at a second position located relatively far from said emission position, and calculating, as a measure of the concentration, $$\text{arctanh}(E_f/E_n),$$

wherein $E_n$ is the energy intensity at said first relatively near position and $E_f$ is the energy intensity at said second relatively far position. In one embodiment $$\text{arctanh}(E_f/E_n)$$

is calculated as $$\tfrac{1}{2} \ln \frac{E_f + E_n}{E_n - E_f}$$

According to a further embodiment, the intensity of the radiation directed into the fluid is suitably controlled by means of the relation $$E_f E_n = 1.$$

Then, a further embodiment of the invention comprises determining the mean value of the measured intensities $E_f$ and $E_n$, and comparing this mean value with 1 in order to determine whether the operation is within the intended measuring range.

An apparatus according to the invention for measuring concentration of particles suspended in a fluid, comprises means for directing radiation energy into the fluid, and means for detecting radiation scattered by the particles and is characterized in that the detecting means comprise first detecting means for detecting the intensity of scattered energy at a position relatively near to an emission position where the radiation energy is directed into the fluid, and second detecting means for detecting scattered energy at a position relatively far from the emission position, and means for calculating, as a measure of the concentration, $$\text{arctanh}(E_f/E_n)$$

wherein $E_n$ is the energy intensity at said first relatively near position and $E_f$ is the energy near intensity at said second relatively far position.

In one embodiment, the means for calculating is arranged to calculate $$\text{arctanh}(E_f/E_n)$$

as $$\tfrac{1}{2} \ln \frac{(E_f + E_n)}{(E_n - E_f)}.$$

The apparatus can to advantage comprise means to control the radiation energy directed into the fluid by means of the relation $$E_f E_n = 1.$$

Then the apparatus could to advantage comprise means for forming the mean value of the measured intensities $E_f$ and $E_n$, and means for comparing this mean value with 1 in order to determine whether the apparatus works in the intended measurement range.

In the inventive apparatus, the radiation energy directed into the fluid could be directed via a first optical fibre, and moreover the scattered radiation could be detected via two sets of opticals fibres, each set being terminated along a circle, said circles being coaxial to the output end of the first fibre. In one embodiment, the fibres of said sets and also the first fibre are terminated in a plane which is normal plane to the first optical fibre, and all the fibres extending in parallel adjacent to said plane.

Other characterizing features of the inventive method and apparatus will be stated in the following, or will be appreciated by the artsmen.

The invention will now be closer defined with reference to the appended drawings.

FIG. 1 shows schematically the principle configuration of an apparatus arrangement according to the invention.

FIG. 2 shows schematically an energy gradient corresponding to the configuration according to claim 1.

FIG. 3 shows the amplitude spectrum of $f(a) = he^{-a}$.

FIG. 4 illustrates the amplitude characterstic of light sent into the suspension, in relation to the distance of the measuring location.

FIG. 5 shows the scattered light function as measured at the near location $E_n$ and at the far location $E_f$.

FIG. 6 shows transmission function and scattered light function in one diagram.

FIG. 7 shows the transmission light field.

FIG. 8 shows the function $E_n \cdot E_f = 1$.

FIG. 9 illustrates graphically the principle method of using coordinate transformation to determine a parameter value A of the contour $E_f = f(E_n)$.

FIG. 10 shows schematically the basic circuitry for calculating an output signal which is proportional to a relatively high particle concentration in a suspension, on the basis of measurement of scattered light measured relatively near and relatively far from the location where the energy is sent into the suspension.

FIG. 11 illustrates the signal contour obtained during operation of the circuitry shown on FIG. 10.

FIG. 12 shows the basic output function characteristic as illustrated for measurement in $SiO_2$.

Figure 13:
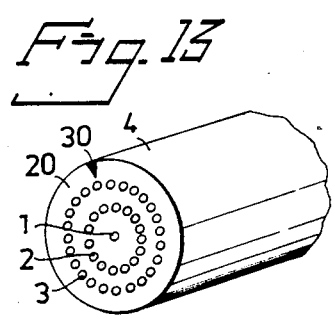
FIG. 13 shows in a perspective view an advantageous arrangement of optical fibres for detecting scattered light at two different distances from the location where light is emitted into the suspension.

The principle design of a basic probe configuration comprises a light source 1 sending out a transmission light beam, and two detectors 2, 3 on different distances, measuring the scattered light, see FIG. 1. In regard to an uncomplicated shape of the probe and a smooth surface, this will preferably be done by measuring backscattered light, as shown in FIG. 1, where the source 1 and the detectors 2, 3 are arranged in a common plane 18 in order to fall in parallel directions into 17, the particle concentration of which is to be measured.

The scattered energy detected by the two detectors, can be utilized to determine the concentration of the material 17, which could be particles suspended in a fluid, for example a liquid such as water.

The result of the following described research is basically an outcome only out of the properties of the e-function nature of transmission light, because this is the primary light falling onto a certain particle location and so the cause of generated scattered ligth, which can be considered as secondary light. The e-function itself offers a wide range of useful mathematical methods to solve physical problems of different subjects. To find a solution is not belonging to the magnitudes in the exponent, because the exponent is dimensionless.

To describe this exponent in physical problems this is always a product of a magnitude and a characteristic value of the system with the inverse dimension. Equivalent to this an absorption function contains a characteristic $e^{AX}$.

A describes the Absorption and X the distance from the light source.

The dimensions have the same basic relationship:

$$\dim (X) = m$$

$$\dim (A) = m^{-1}$$

Basically the e-function is a solution of an oscillation equation. It also can be described by a FOURIER TRANSFORM to get a spectral analysis of amplitudes over the absorption. A coherence between time functions and absorption function is basically given by seeing the light going into the medium like a wave. The enveloping function of the amplitude characteristic over the distance is giving the Lambert-Beer-Law.

Also, on certain locations electrons are oscillating with a special amplitude characteristic. So basically a coherence is to see absorption functions as an amplitude spectrum of local oscillations with the overlapped amplitude decrease of a proceeding wave.

Basically the gradient describes the direction of maximal change of energy over a certain location.

In practice a detector does not see only the response of a point in the medium but a certain part of the volume. So it is detecting a total amount of generated light within this range.

Further, we know that the gradient is a double meaning function having a maximum. So this vector is rotating in the medium, so that it can be supposed, that there is a phase in its function which is responsible for its characteristic.

The gradient over a certain distance can be described by the difference of the amounts of in and outcoming light and so indicates the absorbed light.

Let be $E_o = 1$.

Then the values on the location x and y are:

$$E_x = e^{-Ax}$$

$$E_y = e^{-Ay}$$

So the absorbed energy can be described by:

$$\Delta E = e^{-Ax} - e^{Ay}$$

Now the e-function with a real number exponent can be described by hyperbel functions.

$$e^{-Ax} = \cosh Ax - \sinh Ax$$

$$e^{-Ay} = \cosh Ay - \sinh Ay$$

$$\begin{aligned}\Delta E &= \cosh Ax - \sinh Ax - \cosh Ay + \sinh Ay \\ &= (\cosh Ax - \cosh Ay) + (\sinh Ay - \sinh Ax)\end{aligned}$$

According to the theorems of additions and differences of hyperbel functions this is:

$$\Delta E = 2\sinh\frac{A(x+y)}{2}\sinh\frac{A(x-y)}{2} +$$
$$2\sinh\frac{-A(x-y)}{2}\cosh\frac{A(x+y)}{2}$$
$$= -2\sinh\frac{A(x+y)}{2}\sinh\frac{-A(x-y)}{2} +$$
$$2\sinh\frac{-A(x-y)}{2}\cosh\frac{A(x+y)}{2}$$
$$= 2\sinh\frac{-A(x-y)}{2}\left(\cosh\frac{A(x+y)}{2} - \sinh\frac{A(x+y)}{2}\right)$$
$$= 2e^{-A\frac{x-y}{2}}\sinh A\frac{y-x}{2}$$

So the basic result is:

$$\Delta E = e^{-x} - e^{-y} = 2e^{-A\frac{x+y}{2}}\sinh A\frac{y-x}{2}$$

This equation describes the gradient by an e-function on the middel distance between x and y and an imaginary phase, because hyperbel functions are trigonometric functions with imaginary arguments.

$$\sinh a = -j \sin ja$$

Also the imaginary unit $-j$ describes a rotation in the complex numbers area by $-90$ degrees.
So the expression of the gradient is also:

$$\Delta E = -j2e^{-A\frac{x+y}{2}}\sin jA\frac{y-x}{2}$$

To support this result the FOURIER-INTEGRAL of the e-function can be developed.
A common function will be:

$$f(a) = he^{-a}$$

The value of the spectral function will be:

$$f(b) = \int_o^\infty f(a)e^{-jba}da = \frac{h}{1+b^2} + j\frac{-hb}{1+b^2}$$

The diagram of f is giving the continuous spectrum, see FIG. 3 So the imaginary amplitude spectrum is:

$$Im\, f(b) = h\frac{b}{1+b^2}$$

Now $$\frac{b}{1+b^2}$$

is a rational parameter expression of $$\frac{1}{2}\sin z = \frac{b}{1+b^2}$$

And because of $$\tfrac{1}{2}\sin z = -j\tfrac{1}{2}\sinh z$$

the imaginary becomes $$Im\, f(z) = -j\frac{h}{2}\sinh z$$

and also $$j\, Im\, (z) = \frac{h}{2}\sinh z$$

So the gradient equation represents the imaginary part of the Fourier Transform which means that dispersion in the medium, which is described by the imaginary part of the Fourier Transform, is causing the change of the gradient.

And this dispersion means a change of the refraction index of the medium is according to the absorption.

So following the filed gradient will be the basic field magnitude causing the scattered light function characteristic.

If a light source sends light into a medium, the amplitude characteristic follows the Lambert-Beer-Law over the distance of the measuring location as shown in FIG. 4.

On each location on the beam direction particles are under the influence of energy to generate scattered light.

The nature of scattered light is atomic radiation oscillation. The electrons can be described by the model of a linear oscillator, so that the atoms get a dipol characteristic. Electrons are forced to oscillations under the influence of the E-vector of the infalling electromagnetic light wave.

Looking at certain locations for the amplitude characteristics of scattered light over the absorption is providing the functions shown on FIG. 5. $E_o$, n, and f resp. are constant.

$E_n$ is describing a near location and $E_f$ is describing a far location.

The scattered light function is first increasing in a certain range of low absorption.

It is reaching a maximum and then going down again.

Both the far and the near light have similar characteristics, however, there is a difference in the location of the maximum intensity which is reached earlier on the far light.

The subject of measuring is the decreasing part of the function because this goes to highest concentrations. But to find this solution it needs to describe the complete function in its appearance.

FIG. 6 shows the transmission function and the scattered light function in one diagram.

Following the left side of the scattered light maximum intensity will be called the gain range because increasing absorption generates increasing scattered light. The right side of the maximum will be called attenuation range, because increasing absorption decreases the amplitude of scattered light.

To explain this it needs to look for the dipol nature of the atoms. The intensity of the dipol radiation is dependent from the inducing energy.

Any output response of an induced system is caused by the gradient of the input energy.

Analog to this the induction law in electrotechniques gives a certain understanding for this, where the gradient of a current, for instance, is responsible for the voltage amplitude on the ends of an inductivity.

The responsible gradient for the amount of scattered light is the gradient of transmission light. It indicates absorbed light on certain location which means the available energy for generating scattered light.

FIG. 7 shows how the value of the transmission light field in the absorption range is changing over a small distance between near and far light locations. The diagram shows that the gradient is first increasing reaching a maximum and then decreasing again. The maximum of the gradient means a maximum of absorbed light and so maximum of scattered light intensity.

So at this point, the scattered light function is reaching its top point of the intensity characteristic.

It is of interest to examine the exponent of the e-function in this point.

First the gradient of transmission light is a local function.

$$\frac{d}{dz} E_t = \frac{d}{dz} E_o e^{-Az} = -AE_o e^{-Az} = -|\text{grad } E_t|$$

On a constant location it is also dependent from the absorption:

$$-\frac{d}{dA} |\text{grad } E_t| = -E_o(e^{-Az} - Aze^{-Az})$$

To see the maximum for AZ:

$$E_o(Axe^{-Az} - e^{-Az}) = 0$$

is giving the result:

$$Az = 1$$

Setting this in the exponent means:

$$e^{-Ax} = e^{-1} = 0.368$$

This determines the maximum gradient for the product $Az=1$ and a decrease of local transmission light to an amount of $e^{-1}$ of the light source energy $E_o$. This is also typical for a system constant, for instance, a time constant in dynamic systems.

A basic meaning for a design is, that the top point of the scattered light function, which has the meaning of the low concentration range limit in the attenuation range, can be set to lower concentrations if the distance becomes larger, because the product Az is becoming the value 1 earlier.

The scattered light function is from its nature a double meaning function.

For a certain amplitude it is basically not possible to say if the concentration is in the gain range or in the attenuation range.

Because of the unsymmetrical shape of the curve respectively to the maximum the only unequivocal magnitude is the pair of the values of the far and the near light.

The picture of this pair of values in a coordinate system so is an unequivocal function with the absorption as a parameter, see FIG. 9.

For determination of the absorption parameter, a coordinate system transformation into a certain position can describe it by the according angle.

The related angle functions have to be replaced by hyperbel functions which will be used in the same way. Because of the relationship of trigonometric functions to a circle, hyperbel functions are belonging to hyperbels which indeed have a relationship to circles. So a hyperbel function is describing an angle of a point on a hyperbel locus.

Hyperbel functions are defined for equilateral hyperbels.

In the case of this equation, we make the choice of the coordinate system of the asymptotes of the unit hyperbel. Because of the linear relationship of the scattered values the arrangement will be made for the function:

$$E_n E_f = 1$$

This equation will be the control function for the light source current. It is according to natural curves and also defining the hyperbel. Basically, this is also the law of the constant parallelogram which is in general describing this type of function, see FIG. 8.

To control this product on a constant 1 it is not protected against unsymmetries not belonging to the wanted function.

Unsymmetries can be caused by contamination and reflected transmission light in pipes of a small diameter. Indeed this influence has an effect on low concentrations, if the light source sends high power to the medium.

To get this error down to a minimum and to force reflected transmission light to symetrical amount falling onto the detector circles, the control circuit will be a self leaded system.

$$E_n E_f = 1 \rightarrow E_n = E_f^{-1}$$

This also means that a self-leaded system will always find its lowest level of potential energy.

In order to measure the parameter angle the controlled values $E_n$ and $E_f$ have to be calculated by $$\phi = \text{arctanh} \frac{E_f}{E_n} \quad (\sim \text{absorption})$$

this is the basic equation for getting a linear output response according to the absorption.

Now the artanh can be expressed by:

$$\phi = \text{arctanh} \frac{E_f}{E_n} = \frac{1}{2} \ln \frac{1 + \frac{E_f}{E_n}}{1 - \frac{E_f}{E_n}} = \frac{1}{2} \ln \frac{E_f + E_n}{E_n - E_f}$$

So we have indeed a logarithmic dependence of $\phi$ from the absorption. This function is linear, if the signals are giving the coordinates of a hyperbel according to the equation $E_f E_n = 1$.

The quotient of the sum and the difference is also a compensation for contamination.

A measuring value with additional attenuation can be expressed by a decreasing transmission coefficient.

$$E \rightarrow cE, \quad c \leq 1$$

Because of the common window surface for both detector lines, a contamination will be even.

So we get:

$$\phi = \frac{1}{2} \ln \frac{c(E_f + E_n)}{c(E_n - E_f)} = \frac{1}{2} \ln \frac{E_f + E_n}{E_n - E_f}$$

The quotient is eliminating a contamination error by dividing it out.

The basic circuitry shows the complete measuring principle in a structure diagram, see FIG. 10.

In the basic circuitry shown on FIG. 10, 42 indicates the detector detecting $E_n$, and this signal is fed via a line 52 and to a calculator 60 which provides an output signal 61, (U) corresponding to the concentration. 43 indicates a detector which detects $E_f$, and the signal therefrom is fed via a line 53 into the calculator 60. 52 and 53 are connected to a line 81 via resistors 1 so that the middle potential of the outputs from 42 and 43 are fed into the comparator 80. In the comparator 80, the middle potential is compared to a reference value 82, and the output 83 will indicate whether the output signal 61 refers to a concentration in the intended measurement range.

Moreover, the outputs from detectors 42 and 43 are connected to a control means 70, which is arranged to drive the emitter 41 in response to the relation $E_n \cdot E_f = 1$, as discussed above.

The circuitry shown on FIG. 10 comprises amplifiers and comparators and the like, which are shown in a conventional manner.

Because of the low amplitudes of scattered light a great detecting surface must be developed but this also under the premise of a defined distance. The only geometric figure for this is a circle. If the detectors 2, 3 are on a circle 20, 30 around the light source, the volume of the outcoming light cone will be detected most efficiently.

This is leading to the basic design in FIG. 13.

Light source and detector will be represented by fibres. All fibres of one circle will be bundled leading to a common detector.

The scattered light falling into the fibres of the inner ring is called "near light" and the scattered light falling into the outer ring is called "far light".

This system needs a single calibration procedure. In high concentrations the scattered light signals will ge to a status of constant and equal light amount, which describes a homogeneous light distribution in the medium according to equal gradients on both locations.

At this point the measuring signals are basically defined by the ratio of the number of the fibres on the ring. This is giving a rule for the values of the preamplifier gains of the detectors.

$$\frac{n_f}{n_n} = \frac{v_f}{v_n} \quad \begin{array}{l} n: \text{number of fibres} \\ v: \text{gain of detector signal} \end{array}$$

To adjust tolerances it needs to adjust the difference between the detector signals to zero in a very dark concentration. The kind of medium to do this is not so important, because it needs only a status of homogeneous light distribution.

For this probe this will be made in graphite solution of 3%. (30 g graphite on 1000 ml water).

Overall there is also a possibility now to decide if a concentration is belonging to the gain range or to the attenuation range.

FIG. 11 shows a curve in the coordinate system ($E_n$, $E_f$). This indeed is an unequivocal function for the pairs of values. G is the gravity line of the curve.

So in the gain range all the values are below the ideal function, and in the attenuation range all the values are above the ideal function.

This means, if the product is greater than 1 so the probe is in the measurement range. If the product is below 1 this indicates "out of range". The same effect will be comparing the middle potential of the near and far light signals to 1. This method is shown in FIG. 10.

FIG. 12 shows a typical output function characteristic according to the measuring principle.

Figure 16:
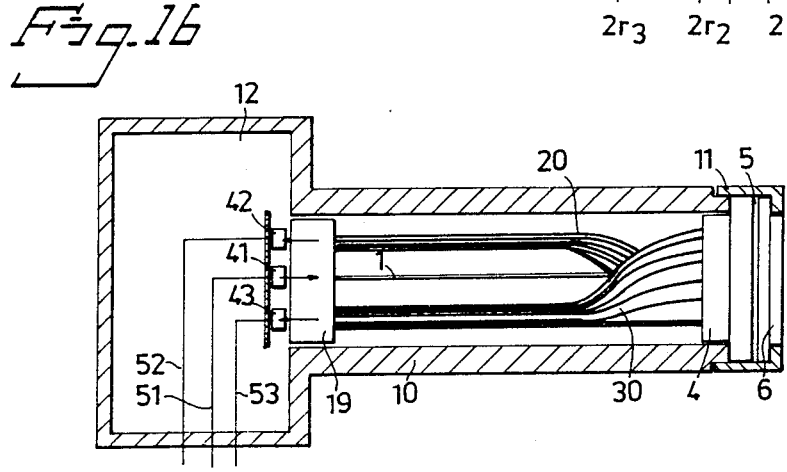
FIG. 16 shows schematically an axial section through a basic probe configuration.

FIG. 16 shows the complete basic shape of the probe. In regard to get a simple configuration, the probe tip 4 will be covered by a flat glass window 6.

The near ends of the fibre bundles are gathered and fixed in a near bundle tip 19 and face resp. detectors 42, 43. Also the near end of fibre 1 is fixed in the tip 19 and faces the emittor 41. The detectors and the emittor are connected via lines 53, 52, 51 to the basic circuitry shown on FIG. 10. The outer end of the probe casing 10 could be provided with a sealing ring 11 so that the interior of the casing is sealed against the environment.

A light beam from the source 41, 1 passing the window 6 will cause internal reflections going back into the detector fibres 2, 3. This makes a fault in measuring.

So to have real back scattered light out of the medium, these reflections have to be eliminated.

A certain distance of the near light ring can avoid this, if the amount of reflected light after some reflections is too small to make a significant error.

This minimum distance is dependent from the used material dimensions and their refractive indexes.

Basically, between the fibre tip surface and the bottom surface of the glass window will be no air slot. But in order to have implemented a very small air slot, which means in practice a source of error in the calculation, the following calculation is considering an air slot 5. The optical fibre tips 1, 2, 3 can be fixed in a glass matrix 4 and the fluid outside the glass window 6 can be assumed to be water.

Figure 14:
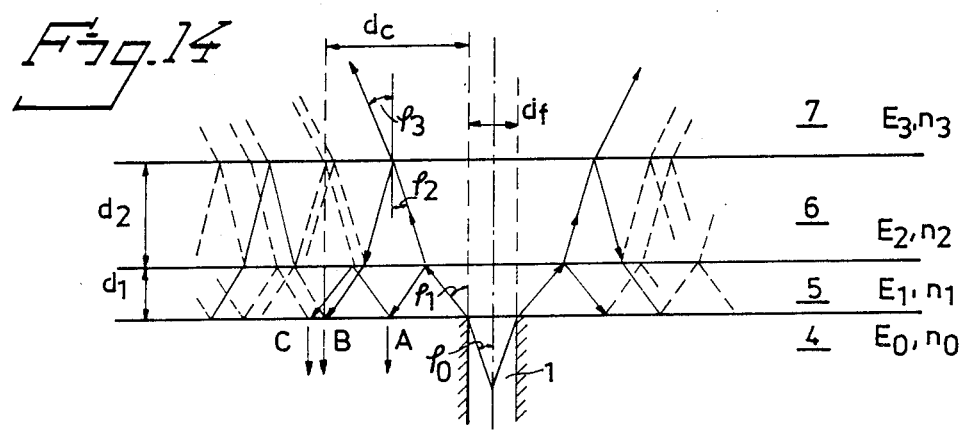
FIG. 14 illustrates schematically a section through the end of a probe according to one embodiment of the invention.

FIG. 14 shows the light paths in this configuration.

A practical calculation with approximated values will show the reflected light profile over the window diameters, which is giving us a basic rule for the radius of the inner circle.

For the calculations a common fibre with an NA of 0.4 will be used.

This is a half acceptance angle of:

$$\phi = 0.5 \arcsin 0.4 = 12°$$

A, B, and C are the points of interest for which we calculate the power rate of infalling energy derived from the output power $E_o$ from the fibre Available values are:

| | |
|---|---|
| $n_0 = n_2 = 1.5$ | $\rho_0 = \rho_2 = 12°$ |
| $n_1 = 1.0$ | $\rho_1 = 18.17°$ |
| $n_3 = 1.33$ | $\rho_3 = 13.56°$ |

Figure 15:
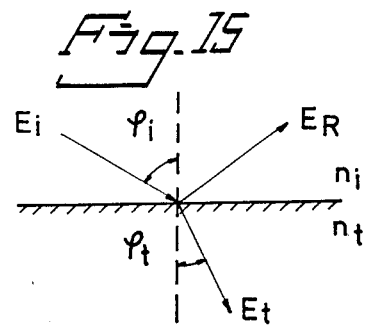
FIG. 15 illustrates schematically energy reflection and transmission at a surface.

The power rate of reflected and transmitted energy on surfaces can be calculated by the FRESNEL-equations. They describe the amplitude and power coefficients for reflection and transmission, which with reference to FIG. 15 are:

amplitude coefficient for reflection:

$$r_\perp = -r_\parallel = \frac{E_R}{E_i} = \frac{n_i \cos\phi_i - n_t \cos\phi_t}{n_i \cos\phi_i + n_t \cos\phi_t}$$

amplitude coefficient for transmission:

$$t_\perp = -t_\parallel = \frac{E_t}{E_i} = \frac{2n_i\cos\phi_i}{n_i\cos\phi_i + n_t\cos\phi_t}$$

power coefficient for reflection: $R = r^2$
power coefficient for transmission: $T = 1 - R$ With these equations we get the following power rates:

| | | |
|---|---|---|
| $R_o = 0{,}046$ | glass ⟷ air | |
| $R_1 = 0{,}46$ | air ⟷ glass | reflected on surface |
| $R_2 = 0{,}004$ | glass ⟷ water | |
| $T_o = 0{,}954$ | glass ⟷ air | |
| $T_1 = 0{,}954$ | air ⟷ glass | transmitted through surface |
| $T_2 = 0{,}996$ | glass ⟷ water | |

The transmitted power rate from the inside of the fibre through into the water is:

$$E_3 = T_2 T_1 T_o E_o = 0.906 \, E_o$$

This means the whole loss of energy from input power into the process in the tip is about 10%.
The power on the points of interest are about:

| | |
|---|---|
| A | $E = 0{,}042 \, E_o$ |
| B | $E = 0{,}038 \, E_o$ |
| C | $E = 8{,}6 \cdot 10^{-5} E_o$ |

This means the distance to point B is the critical distance for high reflected energy power.

For greater distances the power rate has a sharp kink down to $10^{-5}$ of input power.

This value decreases rapidly to larger distances.

This critical distance $d_c$ between the circumferences of two fibres is:

$$d_c = 2d_1\tan\phi_1 + 2d_2\tan\phi_o$$

Figure 17:
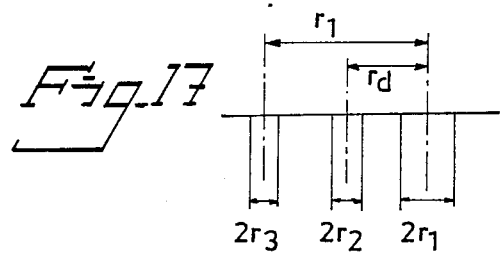
FIG. 17 shows schematically the mutual distances between the three different sets of optical fibres involved in the inventive apparatus.

If we include the radius of the fibres, we get for each radius of the concentric rings according to FIG. 17.

So the critical distance is a basic design value to be sure to get in only scattered light and no significant internal reflected energy.

$$r_d = r_1 r_2 + d_c$$

$$r_i = r_d + r_2 + r_3 + d_c$$

Generally, the probe arrangement should be made to minimize the risk that other energy than that emitted by the emittor and scattered by the particles only, is detected by the detectors. Thus, the arrangement of emittor and detectors should be made to minimize the risk for transfer of energy from emittor to detector directly or by reflection or the like.

I claim:

1. A method of measuring concentration of particles suspended in a fluid, comprising directing radiation energy into to the fluid and measuring the intensity of the energy scattered by the particles, characterized by measuring the intensity at a first position located relatively near to an emission position where energy is directed into the fluid, and also at a second position located relatively far from said emission position, and calculating as a measure of the concentration, $$\text{arctanh}\,(E_f/E_n)$$

wherein $E_n$ is the energy intensity at said first relatively near position and $E_f$ is the energy intensity at said second relatively far position.

2. A method according to claim 1, characterized in that $$\text{arctanh}\,(E_f/E_n)$$

is calculated as $$\tfrac{1}{2} \ln \frac{E_f + E_n}{E_n - E_f}$$

3. A method according to claim 1, characterized by controlling the intensity of the radiation directed into the fluid by means of the relation $$E_f E_n = 1.$$

4. A method according to claim 3, characterized by comparing the mean value of the intensities $E_f$ and $E_n$ with 1 in order to determine whether the operation is within the intending measuring range.

5. Apparatus for measuring concentration of particles suspended in a fluid, comprising means for directing radiation energy into the fluid and means for detecting radiation scattered by the particles, characterized thereby that the detecting means comprise first detecting means for detecting the intensity of scattered energy at a position relatively near to an emission position where the radiation energy is directed into the fluid, and second detecting means for detecting scattered energy at a position relatively far from the emission position, and means for calculating as a measure of the concentration, $$\text{arctanh}\,(E_f/E_n),$$

wherein $E_n$ is the energy intensity at said first relatively near position and $E_f$ is the energy intensity at said second relatively far position.

6. Apparatus according to claim 5, characterized thereby that the means for calculating is arranged to calculate $$\text{arctanh}\,(E_f/E_n)$$

as $$\tfrac{1}{2} \ln \frac{(E_f + E_n)}{(E_n - E_f)}.$$

7. Apparatus according to claim 5, characterized by means for controlling the radiation energy directed into the fluid by means of the relation $$E_f E_n = 1.$$

8. Apparatus according to claim 7, characterized by means for forming the mean value of the detected intensities $E_f$ and $E_n$ and means for comparing this value with 1 in order to determine whether the calculated value corresponds to a concentration in the measuring range.

9. Apparatus according to claim 5, characterized by a first optical fibre for directing the radiation energy into the fluid, and two sets of optical fibres, for transmitting scattered energy to respective detectors, each set of optical fibres being terminated along a circle, said circles being coaxial to the output end of the first fibre.

10. Apparatus according to claim 9, characterized thereby that the fibres of said sets and also the first fibre are terminated in a plane which is normal plane to the first optical fibre, all the fibres preferably extending in parallel adjacent to said plane.

11. A method according to claim 2, characterized by controlling the intensity of the radiation directed into the fluid by means of the relation $$E_f E_n = 1.$$

12. Apparatus according to claim 6, characterized by means for controlling the radiation energy directed into the fluid by means of the relation $$E_f E_n = 1.$$

13. Apparatus according to claim 6, characterized by a first optical fiber for directing the radiation energy into the fluid, and two sets of optical fibers, for transmitting scattered energy to respective detectors, each set of optical fibers being terminated along a circle, said circles being coaxial to the output end of the first fiber.

14. Apparatus according to claim 7, characterized by a first optical fiber for directing the radiation energy into the fluid, and two sets of optical fibers, for transmitting scattered energy to respective detectors, each set of optical fibers being terminated along a circle, said circles being coaxial to the output end of the first fiber.

15. Apparatus according to claim 8, characterized by a first optical fiber for directing the radiation energy into the fluid, and two sets of optical fibers, for transmitting scattered energy to respective detectors, each set of optical fibers being terminated along a circle, said circles being coaxial to the output end of the first fiber.

* * * * *